(12) United States Patent
Klootwijk et al.

(10) Patent No.: US 9,423,375 B2
(45) Date of Patent: Aug. 23, 2016

(54) INTEGRATED CIRCUIT WITH NANOWIRE SENSORS COMPRISING A SHIELDING LAYER, SENSING APPARATUS, MEASURING METHOD AND MANUFACTURING METHOD

(71) Applicant: KONINKLIJKE PHILIPS N.V., Eindhoven (NL)

(72) Inventors: Johan Hendrik Klootwijk, Eindhoven (NL); Marleen Mescher, Eindhoven (NL); Manuel Eduardo Alarcon-Rivero, Eindhoven (NL); Nico Maris Adriaan De Wild, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/435,546

(22) PCT Filed: Oct. 16, 2013

(86) PCT No.: PCT/IB2013/059379
§ 371 (c)(1),
(2) Date: Apr. 14, 2015

(87) PCT Pub. No.: WO2014/060954
PCT Pub. Date: Apr. 24, 2014

(65) Prior Publication Data
US 2015/0293054 A1     Oct. 15, 2015

Related U.S. Application Data

(60) Provisional application No. 61/714,379, filed on Oct. 16, 2012.

(51) Int. Cl.
*G01N 27/414* (2006.01)
*H01L 27/12* (2006.01)
(Continued)

(52) U.S. Cl.
CPC ........ *G01N 27/4146* (2013.01); *H01L 27/1214* (2013.01); *H01L 27/1259* (2013.01);
(Continued)

(58) Field of Classification Search
CPC ............ G01N 27/4146; G01N 27/127; G01N 33/0031; H01L 29/66742; H01L 29/78606; H01L 29/78651; H01L 27/1214; H01L 27/1259; H01L 29/0673
See application file for complete search history.

(56) References Cited

U.S. PATENT DOCUMENTS

| | | |
|---|---|---|
| 2004/0136866 A1 | 7/2004 | Pontis |
| 2006/0078468 A1 | 4/2006 | Gabriel |

(Continued)

FOREIGN PATENT DOCUMENTS

WO    2010120297 A1    10/2010

OTHER PUBLICATIONS

T.S.Y. Moh, S.K. Srivastava, S. Milosavljevic, M. Roelse, G. Pandraud, H.W. Zandbergen, L.C.P.M. De Smet, C.J.M.Van Rijn, E.J.R. Sudholter, M.A. Jongsma, P.M. Sarro, "Silicon Nanowire FET Arrays for Real Time Detection of Chemical Activation of Cells", Micro Electro Mechanical Systems, 2012IEEE 25th Internatioanl Conf. on, IEEE, Jan. 29, 2012, pp. 1344-1347.

*Primary Examiner* — David Vu

(57) ABSTRACT

An integrated circuit (100) comprising a substrate (110); an insulating layer (120) over said substrate; and a first nanowire element (140*a*) and a second nanowire element (140*b*) adjacent to said first nanowire element on said insulating layer; wherein the first nanowire element is arranged to be exposed to a medium comprising an analyte of interest, and wherein the second nanowire element is shielded from said medium by a shielding layer (150) over said second nanowire element. A sensing apparatus including such an IC, a sensing method using such an IC and a method of manufacturing such an IC are also disclosed.

14 Claims, 4 Drawing Sheets

(51) Int. Cl.
*H01L 29/06* (2006.01)
*H01L 29/66* (2006.01)
*H01L 29/786* (2006.01)
*G01N 27/12* (2006.01)
*G01N 33/00* (2006.01)

(52) U.S. Cl.
CPC ...... *H01L29/0673* (2013.01); *H01L 29/66742* (2013.01); *H01L 29/78606* (2013.01); *H01L 29/78651* (2013.01); *G01N 27/127* (2013.01); *G01N 33/0031* (2013.01)

(56) References Cited

U.S. PATENT DOCUMENTS

| | | |
|---|---|---|
| 2006/0263255 A1 | 11/2006 | Han |
| 2006/0270053 A1 | 11/2006 | Tilak |
| 2007/0134866 A1 | 6/2007 | Huang |
| 2008/0210987 A1* | 9/2008 | Bondavalli ......... G01N 27/4146 257/253 |
| 2011/0147802 A1 | 6/2011 | Colli |
| 2011/0221425 A1 | 9/2011 | Bailey |
| 2011/0230759 A1 | 9/2011 | Muller |

* cited by examiner

INTEGRATED CIRCUIT WITH NANOWIRE SENSORS COMPRISING A SHIELDING LAYER, SENSING APPARATUS, MEASURING METHOD AND MANUFACTURING METHOD

This application is the U.S. National Phase application under 35 U.S.C. §371 of International Application No. PCT/IB2013/059379, filed on Oct. 16, 2013, which claims the benefit of U.S. Provisional Application No. 61/714,379 filed on Oct. 16, 2012. These applications are hereby incorporated by reference herein.

FIELD OF THE INVENTION

The present invention relates to an integrated circuit (IC) comprising a substrate; an insulating layer over said substrate; and a first nanowire element and a second nanowire element adjacent to said first nanowire element on said insulating layer.

The present invention further relates to a semiconductor device including such an IC.

The present invention yet further relates to a method of measuring an analyte of interest in a medium using such an IC.

The present invention yet further relates to a method of manufacturing such an IC.

BACKGROUND OF THE INVENTION

The on-going miniaturization of semiconductor technology has enabled a remarkable diversification of functionality embedded in semiconductor devices such as integrated circuits (ICs), which in some cases has led to the provision of near-holistic solutions on a single device. For instance, semiconductor device miniaturization has led to the integration of one or more sensors into a single semiconductor device, and the deployment of such devices can be seen in widely different technical areas, e.g. automotive applications, healthcare applications, industrial gas flue monitoring and so on.

One of the major challenges in providing sensing functionality on an electronic device such as an IC is to ensure that the semiconductor device can be produced in an economically feasible manner. This is for instance a particular challenge when elements of sub-micron dimensions, e.g. nano-elements such as nanowire-based transistors, are to be integrated in the semiconductor device, as it is not at all straightforward to manufacture such nano-elements using processing steps that are compatible with the manufacturing process of the overall semiconductor device. Hence, the integration of such dedicated elements can lead to a significant increase in the complexity of the manufacturing process of the semiconductor device, thereby significantly increasing the cost of such devices.

A particular problem in this respect is that when the sensing medium is a fluid, e.g. a liquid or gas, the sensor arrangement usually requires the presence of a reference sensor or electrode to compensate for sensor drift, i.e. the time-varying response of a sensor to an analyte of interest, which for instance can be caused by the gradual build-up of contaminants on the sensor surface. An example of such an arrangement is disclosed in US 2004/0136866 A1, in which a reference electrode is placed into contact with a fluid to be analysed in order to control the potential of the solution relative to the semiconductor nanowire element.

However, the inclusion of a reference sensor or electrode can further complicate the design of the sensor arrangement, which therefore can further increase the cost of the electronic device. Moreover, the surface of the reference electrode can also be prone to fouling, in which case the sensor readings can become unreliable.

SUMMARY OF THE INVENTION

The present invention seeks to provide an IC according to the opening paragraph in which the need for a separate reference electrode is avoided.

The present invention further seeks to provide a sensing apparatus including such an IC.

The present invention yet further seeks to provide a method of measuring an analyte of interest using such an IC.

The present invention yet further seeks to provide a method of manufacturing such an IC.

The invention is defined by the independent claims. The dependent claims define advantageous embodiments.

In accordance with an aspect of the present invention, there is provided an integrated circuit as defined in the invention.

The present invention is based on the insight that by providing two nanowires adjacent to each other (respective to the flow direction of the medium to be sensed) and providing one of the two nanowires with a shielding layer such as a hydrophobic layer or an anti-ion sheet that prevents the adhesion of particles such as ions or uncharged molecules to the second nanowire and that makes the second nanowire substantially or even completely inert, i.e. insensitive, to the medium, the effects of the gradual build-up of such contaminations on the first nanowire can be filtered out by a differential measurement of the signals originating from these nanowires. In addition, due to the fact that the nanowires are located in the same region of a wafer, i.e. next to each other, the effects of process mismatch that are intrinsically present in sub-micron process technologies can be minimized as such mismatch effects typically are prevalent between different regions of a wafer.

Preferably the second nanowire element is in the direct vicinity of the first nanowire element. More preferably the second nanowire elements are adjacent to each other. Possibly also parallel in their length direction. The closer the nanowire element is to the analyte detection nanowire, the less difference there may be between the medium as sensed by the two nanowires and therewith the better referencing can be.

Each of the nanowires may comprise an oxide surface layer, e.g. by partial oxidation of the nanowire material, which can act as a gate oxide, with the medium acting as a floating gate that provides a gate potential that is a function of e.g., the analyte of interest in the medium.

The differential measurement may be performed off-chip, e.g. by connecting the nanowires to external circuitry via bond pads or the like. Alternatively, the integrated circuit may further comprise a signal processing circuit for processing the respective signals of the first nanowire element and the second nanowire element, which has the advantage that no external circuitry is required to perform the measurement.

In an embodiment, the signal processing circuit comprises a differentiator arranged to subtract the second nanowire element signal from the first nanowire element signal. Such a differentiator, e.g. an inverter or differential amplifier, thus provides an output signal in which the signal of the 'inert' second nanowire has been deducted from the sensing first nanowire. This provides a base signal for the sensing nanowire that can be deducted from any subsequent measurements in order to filter out the effects of the contaminants on the sensing first nanowire.

Preferably, the IC further comprises a first transistor (this may be a Field Effect Transistor (FET)) comprising the first nanowire element and a second transistor (this may be a Field Effect Transistor (FET)) comprising the second nanowire element. The inclusion of a nanowire as the channel of a transistor facilitates a simple and sensitive way of measuring adhesion-induced changes in the impedance of the nanowire.

In an embodiment, the IC comprises an array of transistors wherein each transistor comprises a nanowire extending between a source electrode and a drain electrode, said array including the first transistor and the second transistor. This has the advantage that the presence of many different analytes of interest can be measured simultaneously by respective transistors of the array, e.g. by individual functionalization of the sensing transistors. The respective transistors in said array may share one of a drain electrode and a source electrode, which further simplifies the design of the array.

The substrate may be a silicon on insulator (SOI) substrate. The first nanowire element and the second nanowire element may each comprise a silicon nanowire, e.g. a nanowire formed by patterning the silicon layer of the SOI substrate.

The shielding layer preferably is formed from materials that are readily available in the applicable manufacturing technology of the IC, such as a CMOS technology. For example, the shielding layer may be a dielectric layer such as an oxide or a nitride layer, or instead may be a polymer layer, such as a polyimide or parylene layer. In particular, the shielding layer may be a portion of a suitable photoresist or hard mask material, which may be formed over the second nanowire element using readily available patterning techniques of such materials.

The shielding layer typically has a thickness that ensures that the second nanowire element is insensitive to the medium, such that the signal generated by the second nanowire element reflects the bias applied to the elements, e.g. by the substrate arranged to operate as a backgate. To this end, the substrate preferably is a semiconductor substrate.

In accordance with another aspect of the present invention, there is provided a sensing apparatus comprising a flow channel and the integrated circuit according to an embodiment of the present invention, wherein the first nanowire element and the second nanowire element are arranged in said flow channel such that the first nanowire element and the second nanowire element are adjacent to each other relative to the flow direction of a medium through said flow channel. This has the advantage that the sensor drift and other obscuring effects can be filtered out without the need for a separate reference electrode as previously explained.

In accordance with yet another aspect of the present invention, there is provided a method of measuring an analyte of interest in a medium as defined in the invention. This ensures an accurate measurement of the analyte of interest without the need for a separate reference electrode.

In an embodiment, the step of simultaneously capturing a first nanowire element signal from said first nanowire element and a second nanowire element signal from said second nanowire element comprises driving the first nanowire element and the second nanowire element with an alternating current; and the step of deriving an analyte measurement from the difference between the second nanowire element signal and the first nanowire element signal comprises measuring the complex impedance response of the first nanowire element and the complex impedance response of the second nanowire element to said alternating current. The use of an AC source further enhances the sensitivity of the elements and furthermore enables the detection of a particle of a particular size by applying a frequency sweep as the impedance of the elements will strongly vary at the translational or rotational eigen frequency of the particle.

In accordance with yet another aspect of the present invention, there is provided a method of manufacturing an integrated circuit as defined in the invention. Such a method can be implemented e.g. using CMOS compatible processing steps, such that the IC can be manufactured at relatively low cost.

In an embodiment, the first nanowire element and the second nanowire element each extend from a source region to a drain region, the method further comprising forming an oxide film over each of the first nanowire element and the second nanowire element, e.g. by partial oxidation of the nanowires. This has the advantage that the medium can be used as a floating gate of the elements, e.g. in an embodiment in which the elements each form the channel of a Transistor.

In the invention, a transistor can be a field effect transistor (FET).

BRIEF DESCRIPTION OF THE EMBODIMENTS

Embodiments of the invention are described in more detail and by way of non-limiting examples with reference to the accompanying drawings, wherein:

FIG. 1 schematically depicts an aspect of an IC according to an embodiment of the present invention;

FIG. 2 schematically depicts another aspect of an IC according to an embodiment of the present invention;

Figure 5:
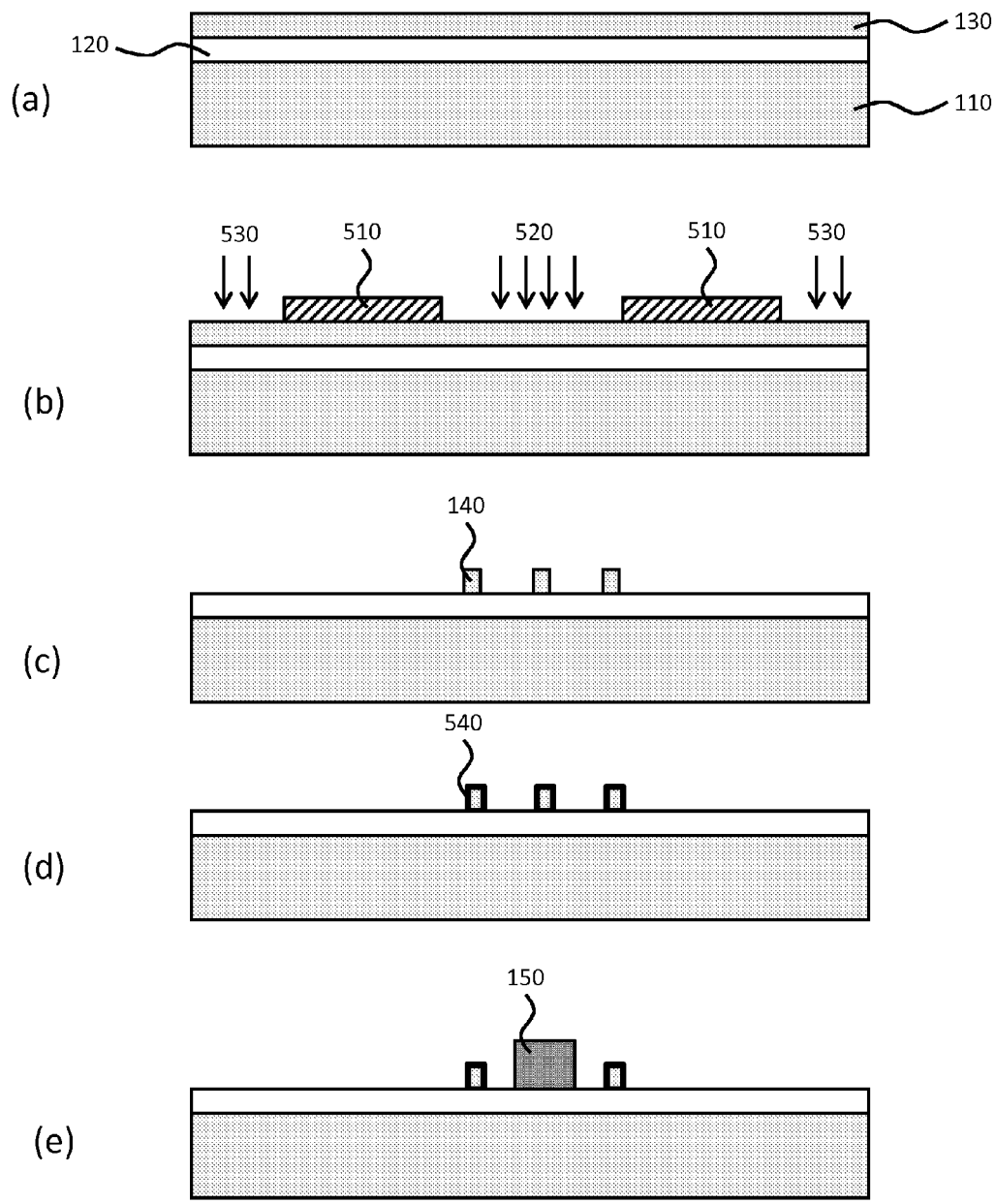
Figure 6:
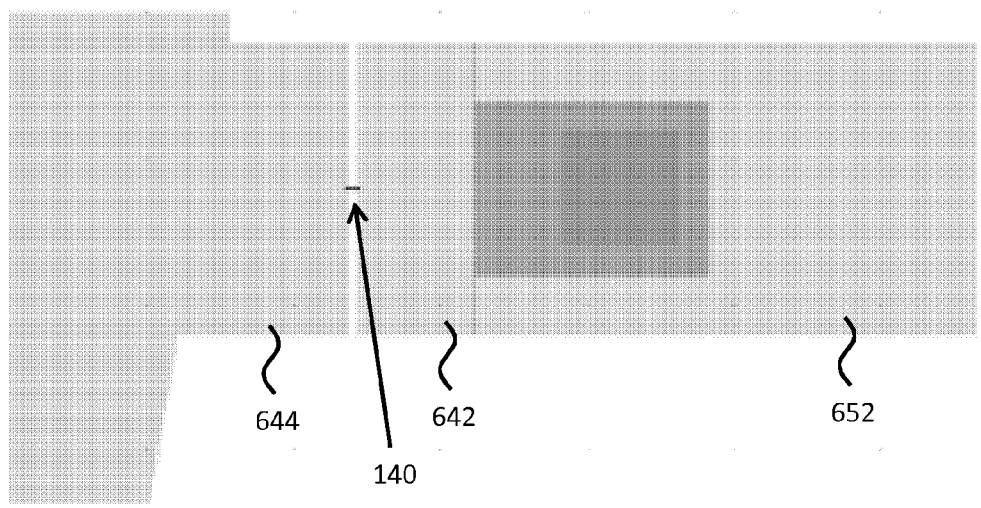

FIG. 5a-e schematically depict an embodiment of a method of manufacturing the IC of the present invention; and FIG. 6 schematically depicts a further aspect of an IC according to an embodiment of the present invention.

DETAILED DESCRIPTION OF THE DRAWINGS

It should be understood that the Figures are merely schematic and are not drawn to scale. It should also be understood that the same reference numerals are used throughout the Figures to indicate the same or similar parts. In the description, embodiments have been described with FETs. These can just as well be replaced with any other transistor. FETs are however easy to integrate.

Figure 1:
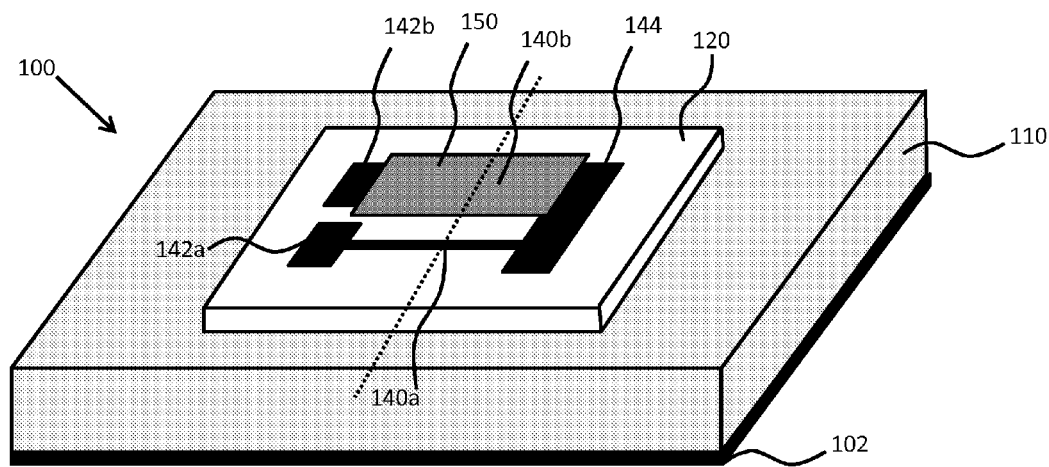

FIG. 1 schematically depicts an IC 100 comprising a silicon substrate 110, a patterned buried oxide layer 120 and a plurality of silicon nanowires, of which two nanowires 140a and 140b are shown, but it should be understood that the IC 100 may comprise a much larger number of such nanowires, which preferably are arranged adjacent to each other in an array. The first nanowire 140a extends between a source region 142a and a drain region 144, whereas the second nanowire 140b extends between a source region 142b and the drain region 144. The first nanowire 140a and the second nanowire 140b thus share a drain region for providing the nanowires with a common drive current, with the individual source regions 142a and 142b allowing measurement of the current through individual nanowires. It should be understood that this arrangement is by way of non-limiting example only; it is equally feasible for the sensing wires to share a source region and have individual drain regions, or to have individual source and drain regions, although the latter complicates the manufacturability of the IC 100 due to the fact that a larger number of contacts to these individual regions has to be provided.

In the context of the present invention, a nanowire is a conductive or semiconductive structure having a cross-section of sub-micron dimensions and having a length that may range from several hundreds of nanometers to several micron. The nanowire may be a solid or hollow structure, and may have a circular or non-circular, e.g. square or rectangular cross-section. By way of non-limiting example, the term 'nanowire' in the present application is intended to include single or multi-walled nanotubes, nanofibers and so on. In a preferred embodiment, the nanowire is a silicon nanowire, which preferably has an oxidized outer surface, as will be explained in more detail later.

The substrate 110 may optionally comprise a back gate 102, e.g. a metallization layer at a surface opposite to the surface on which the buried oxide layer 120 is formed.

Figure 3:
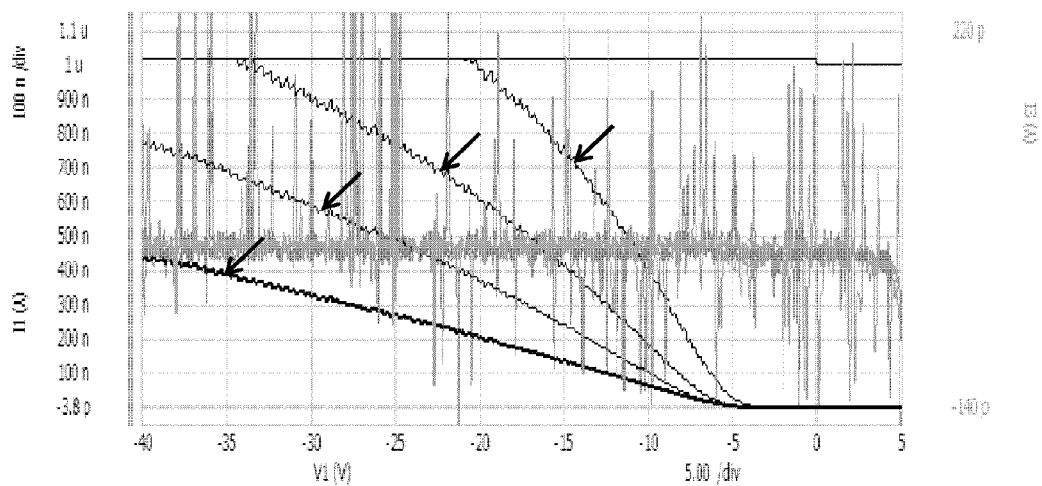
FIG. 3 depicts the current characteristics of four different nanowire sensors of an IC according to an embodiment of the present invention.

In operation, the back gate 102 is used to provide the field effect transistors including the first nanowire 140a and the second nanowire 140b with a bias voltage or bias voltage sweep such that the nanowires are brought into a state of conductivity, e.g. by applying a bias voltage or bias voltage sweep that (at least in part) exceeds the threshold voltage of the nanowires, such that a current will start to run through the nanowires as a function of the driving current applied across the FETs formed by the source regions 142a and 142b, the first and second nanowire 140a and 140b and the common drain region 144. In addition, because the first nanowire 140a is exposed to the medium to be measured, e.g. a fluid such as a liquid sample or a gas flow, the impedance of the first nanowire 140a is a function of the interaction of the first nanowire 140a with the medium. This is demonstrated in FIG. 3, where the current characteristics of four different nanowires as indicated by the arrows are shown. The different inclinations of the current profiles are caused by different interactions with the medium, e.g. different capture event characteristics.

Upon returning to FIG. 1, in case of a first nanowire 140a coated with an oxide film, the oxide film acts as a gate oxide with the medium acting as a gate with a floating gate potential that is dependent of the composition, e.g. ion content, of the medium. The first nanowire 140a may further comprise a functional layer (not shown) for interacting with a specific analyte of interest, in which case the functional layer can be seen as the floating gate, as its potential will be a function of the amount of interaction of the functional layer with the analyte of interest. The above principles are of course known per se e.g. from ChemFETs such as ISFETs and ENFETs and will therefore not explained in further detail for reasons of brevity only.

In contrast, the second nanowire 140b is shielded from the medium by an electrically insulating shielding layer portion 150, which has a thickness that ensures that the impedance of the second nanowire 140b is independent of, i.e. insensitive to, the medium. In an embodiment, the electrically insulating shielding layer portion 150 has a thickness of at least 1 micron. In another embodiment, electrically insulating shielding layer portion 150 has a thickness of at least 5 micron. In yet another embodiment, electrically insulating shielding layer portion 150 has a thickness of at least 10 micron. As will be understood by the skilled person, the required thickness of the electrically insulating shielding layer portion 150 will depend from the material chosen for the electrically insulating shielding layer portion 150. Suitable materials include electrically insulating hydrophobic materials and electrically insulating anti-ion materials, e.g. anti-ion sheets.

Preferably, materials are used for the shielding layer portion 150 that are readily available in or at least compatible with the process technology in which the IC 100 is manufactured, e.g. a CMOS process. For instance, the shielding layer portion 150 may be formed by a selectively deposited or patterned oxide or nitride, e.g. $SiO_2$, $Al_2O_3$, $Si_3N_4$ and so on. Alternatively, the shielding layer portion 150 may be formed by a selectively deposited or patterned resist material, or by a hydrophobic polymer such as parylene or polyimide. Other suitable materials will be apparent to the skilled person.

One of the further advantages of such an electrically insulating shielding layer portion 150 is that any fouling on this material, e.g. due to the gradual build-up of contaminants on the surface of the electrically insulating shielding layer portion 150 exposed to the medium, can also not be sensed by the second nanowire 140b, such that this nanowire is furthermore insensitive to such contamination.

Consequently, the signal produced by the second nanowire 140b is sensitive to the back bias only, such that the influence of the back bias on the signal behaviour of the first nanowire 140a can be filtered out of the response signal of the first nanowire 140a by subtracting the signal of the second nanowire 140b from the signal of the first nanowire 140a.

Figure 2:
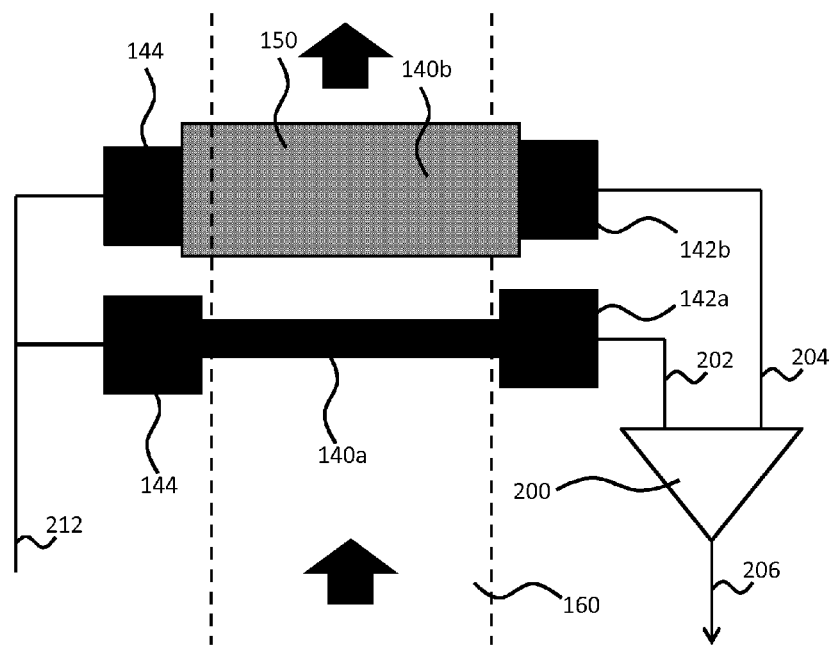

FIG. 2 depicts an example circuit arrangement for this purpose. In this arrangement, the first nanowire 140a and the second nanowire 140b are placed adjacent to each other in a flow channel 160. In operation, the medium flows through the flow channel 160 in the direction indicated by the solid black arrows. From this flow direction, it can be observed that the first nanowire 140a and the second nanowire 140b are placed such that they are exposed to essentially the same flow characteristics. This has the advantage that the risk of different conditions, e.g. temperature differences, flow-related artefacts such as stress or bending, between the nanowires is minimized. Also, by providing the first nanowire 140a and the second nanowire 140b in direct vicinity of each other, process mismatch artefacts, which intrinsically occur between different regions of a single wafer, can be largely ruled out. It is thus ensured that the intrinsic impedance behaviour of the first nanowire 140a and the second nanowire 140b is as near-identical as possible, such that any difference in the impedance characteristics of the first nanowire 140a and the second nanowire 140b are medium-induced.

To this end, the first source region 142a and the second source region 142b may be connected to a differentiating circuit 200 via respective conductors 202 and 204. The differentiating circuit or differentiator 200 is arranged to produce the difference between the signal from the first nanowire 140a and the signal from the second nanowire 140b on its output 206, e.g. by subtracting the signal from the second nanowire 140b from the signal from the first nanowire 140a. Such circuits are known per se and any suitable implementation of such a differentiator 200, e.g. a differential amplifier or inverter, may be chosen. Typically, two differential measurements will be performed, one before and one after an analyte capture event, such that the difference between these two measurements, e.g. the measured difference in the impedance of the first nanowire 140a, can be interpreted to characterize the type and/or amount of material deposited on the first nanowire 140a.

In an embodiment, the differentiating circuit 200 is located external to the IC 100, in which case the conductors 202 and 204 may be connected to respective bond pads of the IC 100, each bond pad providing a conductive connection to one of the source regions 142a and 142b. In an alternative embodiment, the differentiating circuit 200 forms part of the IC 100, in which case the conductors 202 and 204 for instance may be located in the metallization stack of the IC. Many other suitable arrangements will be immediately apparent to the skilled person.

The aforementioned differential measurement may also be used to establish the level of contamination of the exposed surface of the first nanowire 140*a* or at least to calibrate the first nanowire 140*a*. To this end, a first calibration differential measurement may be performed, during which a fluid with a known composition, e.g. a calibration fluid, is flowed over the array of nanowires including the first nanowire 140*a* and the second nanowire 140*b*. The differential signal can be linked to the known composition as is common in the process of calibration. If the analyte of interest is absent in the known composition, the differential signal D1 can be indicative of the level of contamination that has built up at the exposed surface of the first nanowire 140*a*.

A subsequent differential measurement D2 of a sample flowing of the nanowire array can be correlated to calibration differential measurement D1 in any suitable manner, e.g. by subtracting D1 from D2 in case D1 is indicative of the level of contamination on the exposed surface of the first nanowire 140*a*. To this end, a signal processor (not shown) may be coupled to the output 206 of the differentiating circuit 200, which signal processor is adapted to perform the aforementioned correlation. The signal processor is typically adapted to at least store the latest value of D1, to which end the signal processor may include or have access to a data memory. The signal D1 may be stored in digital form, in which case the signal processor may be coupled to the output 206 via an analog to digital converter (not shown). The signal processor typically comprises an output for providing the correlation result such that a user of the IC 100 or a sensing apparatus including the IC 100 can interpret this correlation result. The signal processor may be external to the IC 100 or may form part of the IC 100.

Figure 4:
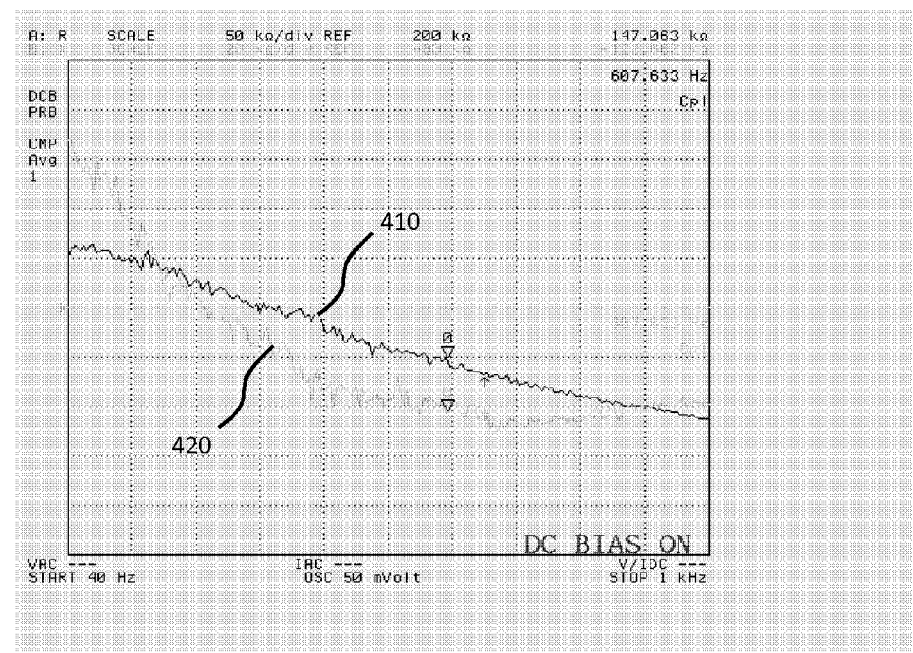
FIG. 4 depicts the complex impedance of a nanowire sensor on an IC according to an embodiment of the present invention when driven by an AC source.

The drive current applied to the shared drain 144 of the array of nanowires including the first nanowire 140*a* and the second nanowire 140*b* via the conductor 212 may have any suitable form, e.g. a direct current or an alternating current. In case of the application of an alternating current, the impedance of the nanowires will have a complex form, i.e. comprise a real and an imaginary part. This further enhances the selectivity of a sensing nanowire such as the first nanowire 140*a*, and further facilitates the detectability of materials or particles of a particular size due to the fact that the impedance will exhibit a large variation when the alternating current matches the resonance or Eigen frequency of the translational or rotational modes of the particles. An example of a decomposed complex impedance characteristic of a nanowire driven with an alternating current is shown in FIG. 4, which includes a real component 410 and an imaginary component 420.

An example method of manufacturing such an IC 100 is schematically depicted in FIG. 5. In step (a), a substrate 110 is provided that carries an electrically insulating layer 120 and a semiconductor material layer 130. Preferably, this arrangement is provided as a silicon on insulator substrate in which layers 110 and 130 are silicon layers separated by a buried oxide layer 120, but it should be understood that the layer stack as shown in step (a) may be provided in any suitable manner using any suitable materials. A metal contact 102 (not shown) may also be present or formed at any suitable point in the method to provide the substrate 110 with a back gate contact such that the substrate 110 can be used as a back gate.

In a next step (b), a patterned mask 510 is formed on the silicon layer 130 that defines the regions into which impurities are to be implanted, after which such impurities are implanted into the silicon layer 130, such as impurities 520, e.g. N$^-$-type impurities, in the region in which the nanowires 140 are to be formed and impurities 530, e.g. N++-type impurities, in the source and drain regions 142 and 144. As the formation of such a mask and such implantation steps are routine practice for the skilled person, they will not be explained in any further detail for the sake of brevity only.

Subsequently, the mask 510 is removed from the silicon layer 130, which is subsequently patterned to form the nanowires 140 and the source and drain regions 142 and 144, as shown in step (c). It is noted that the cross-section of the IC 100 shown in step (c) is the cross-section indicated by the dashed line in FIG. 1, which is rotated 90° compared to the cross-sections shown in step (a) and (b), such that the formed source and drain regions 142 and 144 are not shown in the cross-section of step (c). The patterning of the silicon layer 130 may be achieved in any suitable manner. Particularly preferred is the use of electron beam lithography to form the nanowires 140, which may be combined with a dry etch to form the source regions 142 and the drain region(s) 144.

Step (d) is an optional step, which is however preferred to ensure that the medium to which the nanowires 140 are exposed acts as a floating gate on the channel regions of the field effect transistors defined by the nanowires 140. In step (d), the nanowires are provided with an oxide layer 540. In case of silicon nanowires 140, this is preferably achieved by the partial oxidation of the silicon, e.g. by exposing the silicon nanowires 140 to an oxide-rich environment at elevated temperatures, e.g. 300° C. or higher for a period of time. This oxide layer 540 thus acts as a gate oxide when the nanowires 140 are brought into contact with the medium.

Next, selected nanowires 140 are covered in the shielding layer portion 150 to shield them from exposure to the medium to be measured, as previously explained. The one or more shielding layer portions may be formed in any suitable way, e.g. by deposition of a shielding layer over all nanowires 140 and the selective removal of the shielding layer material from those nanowires 140 that are to be used as sensing nanowires, or alternatively by the selective deposition of the shielding layer over only those nanowires 140 that are to be shielded from the medium to be measured. Due to the fact that the spacing between nanowires 140 is many factors larger than the cross-section or thickness of a single nanowire 140, such a selective deposition can be achieved using techniques that are routinely available to the skilled person.

FIG. 6 schematically depicts a top view of a single FET including source contact 642, drain contact 644, the metal 652 in conductive contact with the source contact 642 (the metal contacting the drain contact has been omitted for the sake of clarity) and the nanowire 140. This clearly demonstrates that there is ample room for the selective deposition of the shielding layer 150 over the nanowire 140.

Any suitable number of shielded nanowires 140*b* may be present in the array of nanowires 140 on the IC 100. For instance, each sensing nanowire 140*a* may have its own shielded nanowire 140*b*, such that the array comprises an [ab]$_n$ pattern, in which a and b respectively represent sensing nanowire 140*a* and shielded nanowire 140*b*, and in which n is a positive integer. In case of n=1, the array comprises only two nanowires 140, i.e. the first nanowire 140*a* and the second nanowire 140*b*, but it should be understood that n may adopt much larger values, e.g. n=50, n=500 and so on. In an alternative embodiment, a shielded nanowire 140*b* is shared by two sensing nanowires 140*a* on either side of the shielded nanowire 140*b*, such that the array exhibits a pattern [aba]$_n$, which has the advantage that a higher percentage of the nanowires 140 in the array are sensing nanowires. A shielded nanowire 140*b* may be shared by any number of sensing nanowires 140a such that the array may exhibit any suitable repetitive pattern or no pattern at all, although it is preferred that the sensing nanowires 140a are located in close vicinity to their shielded nanowire 140b for reasons already explained above.

The IC 100 may be integrated in any suitable sensing apparatus. Such a sensing apparatus typically comprises a flow channel 160 as shown in FIG. 2, which may have any suitable dimension. The IC 100 is typically placed such that the first sensing nanowire 140a and the shielded nanowire 140b are exposed in the flow channel as shown in FIG. 2, i.e. by ensuring that both nanowires are exposed to essentially the same flow characteristics in order to minimize the risk of flow-induced differences in nanowire behaviour. Such a sensing apparatus may for instance be a microfluidics-based sensing apparatus or an assay-based sensing apparatus to be used in a healthcare application, an exhaust gas sensing apparatus to be used in an industrial or automotive application and so on. Many other suitable application domains for such a sensing apparatus will be apparent to the skilled person.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An integrated circuit comprising:
   a substrate;
   an insulating layer over said substrate; and
   a first nanowire element and a second nanowire element on said insulating layer wherein
   the first nanowire element is a source node of a first transistor and the second nanowire element is a source node of a second transistor, said first transistor and said second transistor having a common drain node,
   wherein the first nanowire element is arranged for exposure to a medium comprising an analyte, and wherein the second nanowire element is arranged to be shielded from said medium by a shielding layer over said second nanowire element.

2. The integrated circuit of claim 1, wherein each of the first nanowire element and the second nanowire element are covered by an oxide film, the shielding layer being arranged on said oxide film.

3. The integrated circuit of claim 1, further comprising a signal processing circuit for processing the respective signals of the first nanowire element and the second nanowire element.

4. The integrated circuit of claim 3, wherein the signal processing circuit comprises a differentiator arranged to subtract the second nanowire element signal from the first nanowire element signal.

5. The integrated circuit of claim 1, further comprising an array of said first transistor and said second transistor.

6. The integrated circuit of claim 1, wherein the substrate is a semiconductor substrate arranged to provide a bias voltage to the first nanowire element and the second nanowire element.

7. The integrated circuit of claim 1, wherein the first nanowire element and the second nanowire element each comprise of a silicon nanowire.

8. The integrated circuit of claim 1, wherein the shielding layer has a thickness that ensures that the second nanowire element is insensitive to the medium.

9. The integrated circuit of claim 1, wherein the shielding layer comprises a dielectric layer such as an oxide layer or a nitride layer or a polymer layer, said polymer layer being of: a polyimide layer or a parylene layer.

10. A sensing apparatus comprising a flow channel and the integrated circuit of claim 1, wherein the first nanowire element and the second nanowire element are arranged in said flow channel such that the first nanowire element and the second nanowire element are adjacent to each other relative to the flow direction of a medium through said flow channel.

11. A method of measuring an analyte of interest in a medium, the method comprising:
   providing an integrated circuit according to claim 1;
   flowing said medium over the first nanowire element and the second nanowire element in a direction such that the first nanowire element and the second nanowire element are adjacent to each other relative to said flow direction;
   simultaneously capturing a first nanowire element signal from said first nanowire element and a second nanowire element signal from said second nanowire element; and
   deriving an analyte measurement from the difference between the second nanowire element signal and the first nanowire element signal.

12. The method of claim 11, wherein:
   the step of simultaneously capturing a first nanowire element signal from said first nanowire element and a second nanowire element signal from said second nanowire element comprises driving the first nanowire element and the second nanowire element with an alternating current; and
   the step of deriving an analyte measurement from the difference between the second nanowire element signal and the first nanowire element signal comprises measuring the complex impedance response of the first nanowire element and the complex impedance response of the second nanowire element to said alternating current.

13. A method of manufacturing an integrated circuit, comprising:
   providing a substrate, an insulating layer on said substrate and a semiconductor layer on said insulating layer;
   patterning the semiconductor layer to form a first nanowire element as a source node of a first transistor and a second nanowire element adjacent to said first nanowire element on said insulating layer, said second nanowire element being a source node of a second transistor, wherein said first transistor and said second transistor share a common drain node; and
   depositing an shielding layer over the second nanowire element only.

14. The method of claims 13, comprising:
   forming an oxide over each of the first nanowire element and the second nanowire element prior to depositing said shielding layer.

* * * * *